United States Patent
Khalili et al.

(10) Patent No.: US 11,844,535 B2
(45) Date of Patent: *Dec. 19, 2023

(54) DUAL COUPLING REAMER HANDLE

(71) Applicant: VIANT AS&O HOLDINGS, LLC, Foxborough, MA (US)

(72) Inventors: Farid B. Khalili, Briarcliff Manor, NY (US); Archie Newsome, Mentone, IN (US); Jack Bryant, Warsaw, IN (US)

(73) Assignee: VIANT AS&O HOLDINGS, Foxborough, MA (US)

( * ) Notice: Subject to any disclaimer, the term of this patent is extended or adjusted under 35 U.S.C. 154(b) by 121 days.

This patent is subject to a terminal disclaimer.

(21) Appl. No.: 16/901,810

(22) Filed: Jun. 15, 2020

(65) Prior Publication Data
US 2020/0305895 A1 Oct. 1, 2020

Related U.S. Application Data

(63) Continuation of application No. 16/032,188, filed on Jul. 11, 2018, now Pat. No. 10,682,149.

(51) Int. Cl.
*A61B 17/16* (2006.01)
*A61B 17/3207* (2006.01)
*A61B 17/00* (2006.01)

(52) U.S. Cl.
CPC ........ *A61B 17/1659* (2013.01); *A61B 17/164* (2013.01); *A61B 17/320758* (2013.01); *A61B 17/1677* (2013.01); *A61B 2017/00367* (2013.01); *A61B 2017/00464* (2013.01); *A61B 2017/00469* (2013.01); *A61B 2017/00473* (2013.01); *A61B 2017/00477* (2013.01)

(58) Field of Classification Search
CPC ... A61B 17/16; A61B 17/1659; A61B 17/164; A61B 17/32; A61B 17/3207
See application file for complete search history.

(56) References Cited

U.S. PATENT DOCUMENTS

| | | | |
|---|---|---|---|
| 9,050,110 B2 * | 6/2015 | Cannell | B25G 3/24 |
| 9,414,848 B2 * | 8/2016 | Edwards | A61B 17/162 |
| 10,231,741 B2 * | 3/2019 | Crandall | A61B 17/162 |

(Continued)

OTHER PUBLICATIONS

International Search Report and Written Opinion dated Oct. 1, 2019 related to corresponding International Appl No. PCT/US19/41392.

(Continued)

*Primary Examiner* — Christopher J Beccia
(74) *Attorney, Agent, or Firm* — Grossman, Tucker, Perreault & Pfleger, PLLC

(57) ABSTRACT

A surgical tool handle comprising a tool attachment coupling having locking piston subassembly is described. The attachment coupling is designed with a bayonet-type fitting having a series of coupling grooves constructed to accept surgical cutting tools having an attachment member of different cross-sectional geometries. More specifically, the attachment coupling comprises a coupling groove that accepts tool attachment members having both curved and rectangular cross-sectional geometries. In addition, a locking piston subassembly biases against the surgical tool attachment member received in the coupling groove to further stabilize the tool during a surgical procedure.

14 Claims, 9 Drawing Sheets

(56) References Cited

U.S. PATENT DOCUMENTS

| 10,682,149 B2* | 6/2020 | Khalili ................. A61B 17/162 |
| 2003/0216716 A1 | 11/2003 | Desarzens |
| 2012/0023733 A1 | 2/2012 | Cannell et al. |
| 2015/0313610 A1 | 11/2015 | Edwards et al. |
| 2017/0000499 A1 | 1/2017 | Crandall et al. |
| 2017/0303936 A1 | 10/2017 | Weekes et al. |
| 2018/0153560 A1 | 6/2018 | Chenaux et al. |

OTHER PUBLICATIONS

Extended Search Report from related European Appln. No. 219834080. 4, dated Mar. 7, 2022.

* cited by examiner

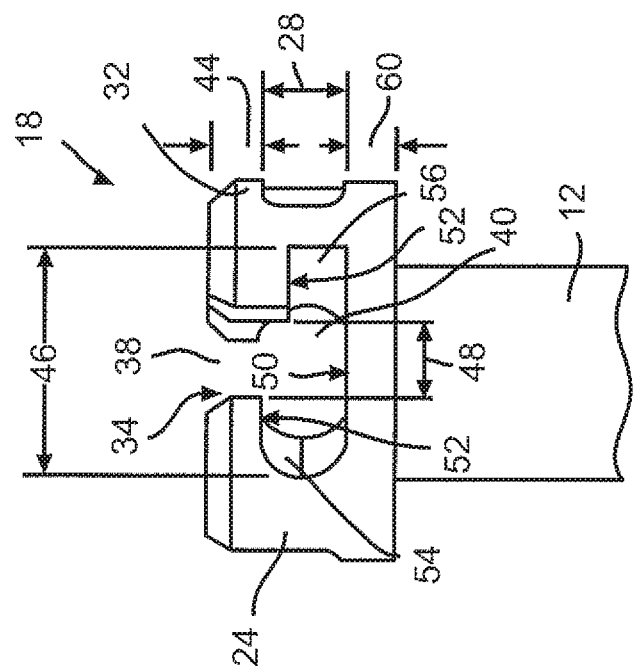
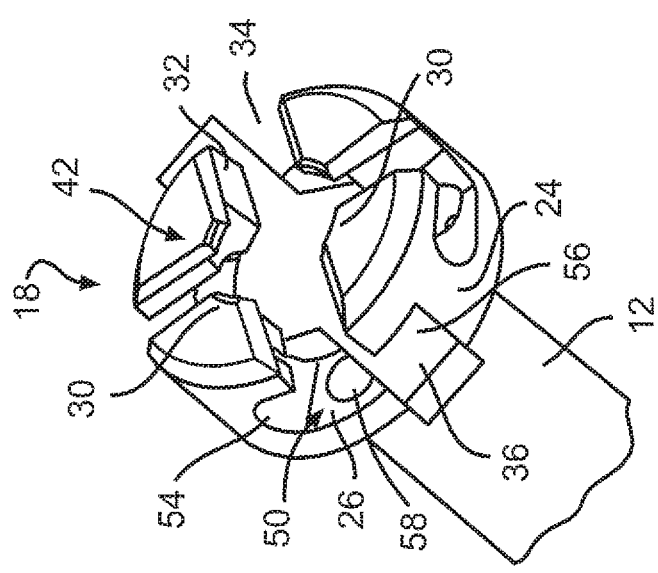

DUAL COUPLING REAMER HANDLE

CROSS REFERENCE TO RELATED APPLICATIONS

This application is a continuation application of U.S. non-provisional application Ser. No. 16/032,188, filed Jul. 11, 2018, the entire disclosure of which is incorporated herein by reference.

FIELD

This invention relates to surgical tool handles, and more particularly, to handles for rotary surgical cutting tools.

BACKGROUND

Surgical cutting tools such as orthopedic reamers and patella cutters are used extensively in a variety of surgical procedures to cut bone and tissue. In many cases, because of the high cost of these surgical cuttings tools they are often reused from patient to patient. Therefore, in order to minimize risk of infection or disease, it is important that these surgical tools and their respective holders be kept clean and sterile before any use in a surgical procedure.

A surgical tool, for example for preparing the acetabulum for a hip prosthesis, works in a medium that can cause considerable soiling of the tool and its handle. Despite the importance of doing so, thorough cleaning of these devices is difficult. Surgical tool handles of the prior art are designed such that washing and rinsing are generally not an effective way of cleaning the tool. This is typically due to the small spaces left between component parts which allow only minimal access by cleaning agents. Therefore, to improve the effectiveness of cleaning the surgical tool, it is often desirable to construct these cutting tools such that the cutting end is detachable from its handle. Thus, by removing the handle from the cutting end, a more thorough cleaning is generally achieved.

In addition, during a surgical procedure, it is also often desirable to interchange a tool handle with a variety of cutting devices. The ability to connect a handle with a variety of different cutting devices provides the surgeon with increased flexibility in removing tissue and bone. However, since cutting tools, such as reamers, often comprise many different handle connection interfaces, there is a need to provide a tool handle that is capable of securely attaching to a variety of different cutting tools. For example, some surgical cutting tools have a handle connection interface or attachment member comprising a crossbar with a curved or round cross-section while others may comprise an attachment member having a rectangular cross-section. Therefore, there is a need to securely connect a cutting tool of a variety of different attachment member geometries to a handle to facilitate manipulation of the tool within the body.

Furthermore, during surgical use a significant amount of stress and pressure is often applied to the reamer tool to facilitate cutting of bone and/or tissue. Because of this, it is important for the reamer and other surgical cutting tools to remain solidly secured to its handle as the tool is manipulated within the body. If, for example, the reamer or other cutting tool were to move or become loose from its handle, bone or tissue may be unintentionally cut. Therefore, it is important to minimize movement or play of the cutting end portion connected to a handle as unexpected movement of the cutting tool may result in undesirable surgical complications to the patient. For example, a handle designed to receive a cutting tool having an attachment member of a curved cross-sectional geometry generally cannot receive and secure a cutting tool comprising an attachment member of a rectangular cross-section.

Typically, existing tool handles are designed to connect to a surgical cutting tool having an attachment member of a specific geometry. Generally, these handles are designed to connect a surgical cutting tool having an attachment member of either a round cross-section or a rectangular cross-section, but not both.

U.S. Pat. No. 7,115,119 to Desarzens, the contents of which are incorporated herein and, in addition, which is assigned to the assignee of the present invention, discloses a tool handle comprising a tool coupling designed to receive a surgical tool having a tool attachment member of either a round cross-section or a rectangular cross-section. As shown in FIG. 2 of the '119 patent to Desarzens, the attachment coupling comprises a recess having both a rectangular and a curved shaped portion. More specifically, a portion of the recess opening is designed to have both a rectangular and a curved cross-section so that a tool attachment member of either a round cross-section or a rectangular cross-section can be received. Spring loaded collar pins positioned within the perimeter of the base of the coupling provide support for the attachment member when positioned within the coupling.

While the tool coupling described by the '119 patent to Desarzens is acceptable for connecting to cutting tools having both curved and rectangular cross-sectional attachment geometries, additional work has been performed to develop a tool handle locking mechanism that during use further minimizes movement and play of the surgical tool connected to the handle. In addition to providing a tool handle with an improved locking mechanism, the surgical tool handle of the present invention provides structure for connecting to cutting tools having attachment members of both rectangular and curved cross-sectional geometries separately or simultaneously. Thus, the present invention provides an improved tool handle that minimizes movement and play of a connected cutting tool during use, thereby providing a robust connection between the tool and the handle.

SUMMARY

A surgical tool handle aids a surgeon in controlling the use of a cutting tool during surgery, for example, during preparation of a femoral cavity for reception of a hip joint prosthesis. The present invention describes such a surgical tool handle, but is adapted to secure cutting tools having a variety of attachment members of different cross-sectional geometries. That way, the present tool handle allows for secure attachment of a multitude of cutting tools regardless whether their attachment member has a round and/or rectangular cross-section.

The present surgical handle comprises a shaft providing an end onto which the attachment member of a surgical tool is coupled. The shaft extends from a proximal shaft end to a distal shaft end supporting a coupling. The distal coupling comprises a bayonet fitting in which the attachment member of a cutting tool such as a reamer can be attached. The distal coupling is designed with sidewall openings comprising both round and rectangular cross-sections that are spaced apart from each other, thereby enabling surgical tool attachment members of both geometries to be received at one time, if desired.

A slidable collar positioned on the shaft provides a series of collar pins that impinge and secure the attachment member of the surgical tool within the coupling of the surgical handle. In addition, the attachment member of the surgical tool is further secured to the distal end of the shaft using a piston that resides within an end of the shaft. A bias member residing circumferentially around the body of the piston provides a bias force that helps secure the attachment member within the coupling of the surgical handle. This attachment mechanism of the present invention provides a secure, but removable means of attaching a cutting tool or reamer to a reamer handle.

These features of the present invention will be apparent upon consideration of the following detailed description in connection with the following drawings.

BRIEF DESCRIPTION OF THE DRAWINGS

FIG. 3 is a perspective view of an embodiment of the coupling for the surgical handle shown in FIG. 1 receiving an attachment member of a rectangular cross-section.

FIG. 3A is a side elevational view of the coupling of the surgical handle shown in FIG. 1 without the attachment member of a surgical tool.

DETAILED DESCRIPTION

Figure 1:
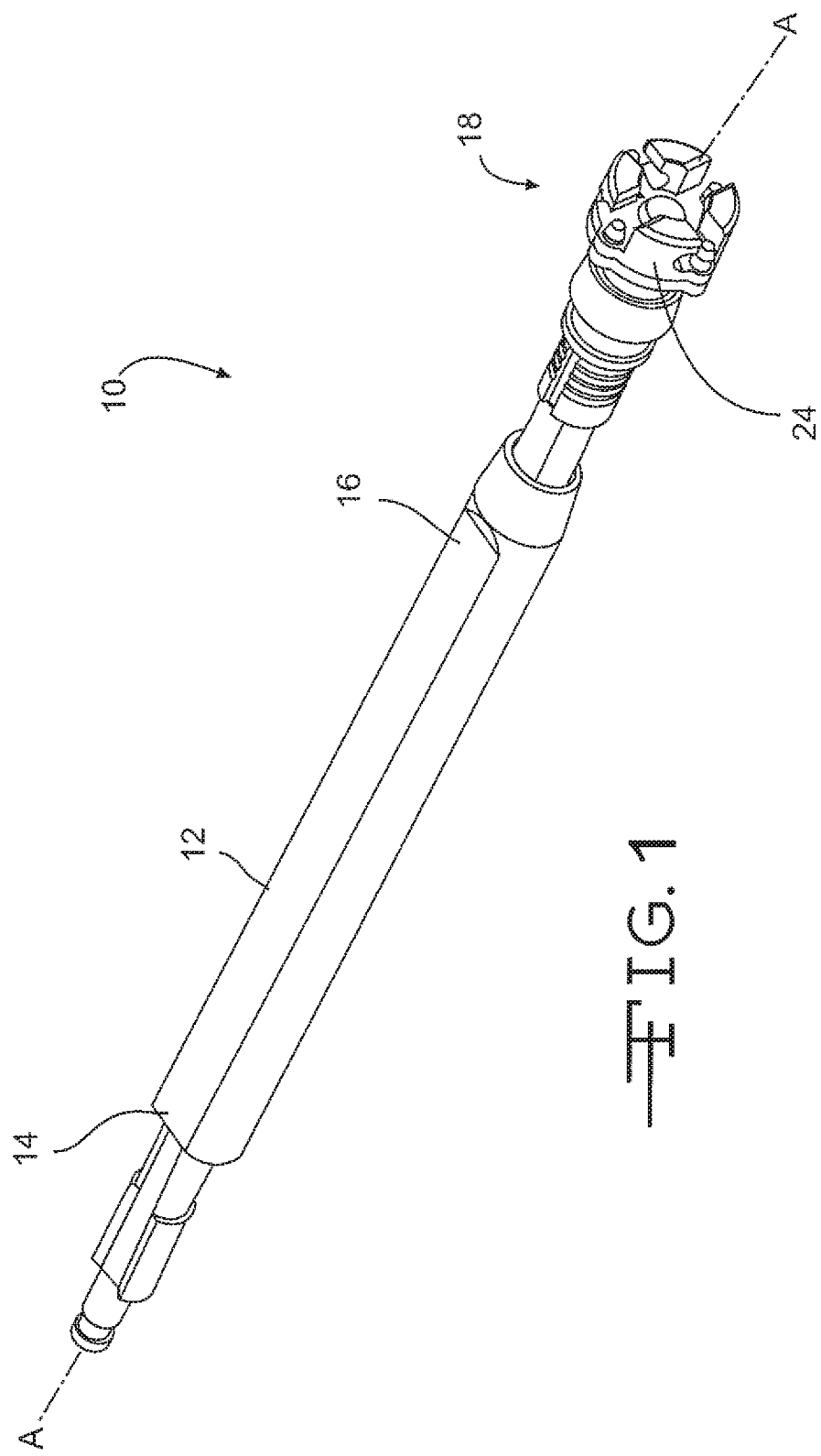
FIG. 1 is a perspective view of an embodiment of a surgical tool handle assembly of the present invention.
Figure 1A:
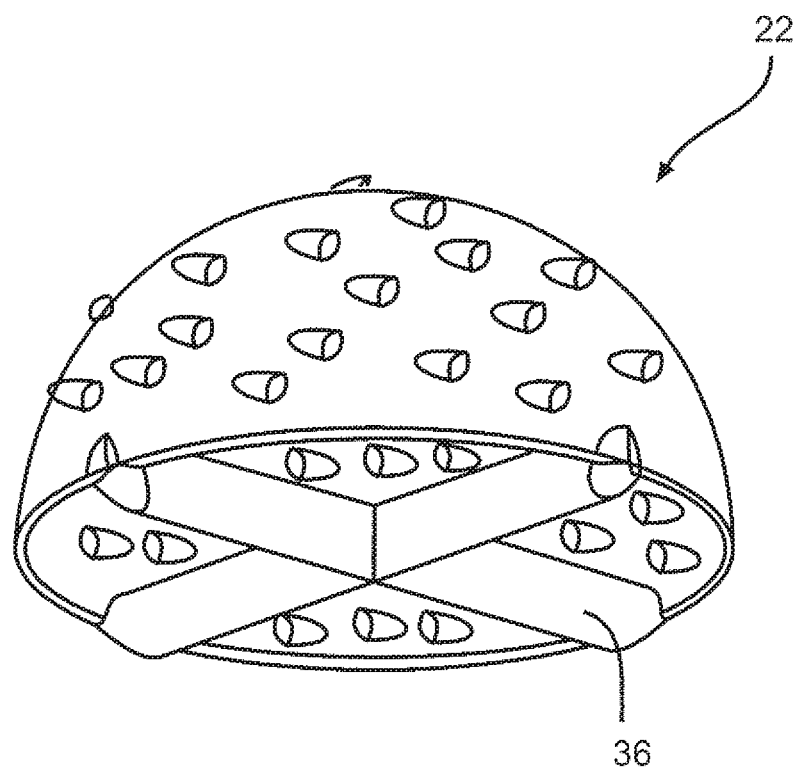
FIGS. 1A and 1B illustrate embodiments of a surgical tool having different attachment member cross-sectional geometries.
Figure 1B:
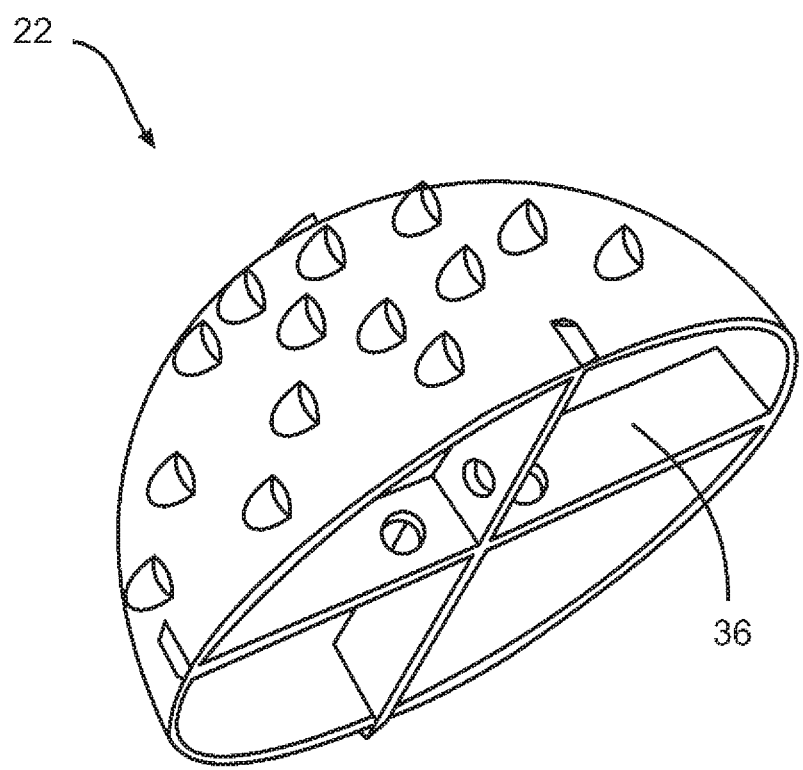

Referring now to the drawings, FIG. 1 illustrates an embodiment of a surgical tool handle 10 of the present invention. As shown, the surgical tool handle 10 comprises a shaft 12 extending along a longitudinal axis A-A from a shaft proximal portion 14 to a shaft distal portion 16. A coupling 18 is connected to an end of the shaft distal portion 16. A handle locking mechanism 20 (FIG. 7) is also provided. The coupling 18 is connectable to a surgical tool 22, such as a reamer, a patella cutting tool, a rasp or a broach, to enable controlled manipulation of that tool. FIGS. 1A and 1B illustrates embodiments of an orthopedic reamer 22 having different attachment member cross-sectional geometries. It is noted that while FIGS. 1A and 1B illustrate embodiments of an orthopedic reamer, the surgical tool handle 10 of the present invention may be used with a variety of non-limiting surgical tools.

FIGS. 2, 3, 3A, 4, 4A, 5 and 5A illustrate embodiments of the coupling 18 comprising an annular sidewall 24 that extends outwardly from a platform 26. The annular sidewall 24 preferably extends circumferentially around an imaginary longitudinal axis A-A. In addition, the annular sidewall 24 is preferably spaced from longitudinal axis A-A. In a preferred embodiment, a length 28 of the sidewall 24 extends distally along the axis from the coupling platform 26.

Figure 2:
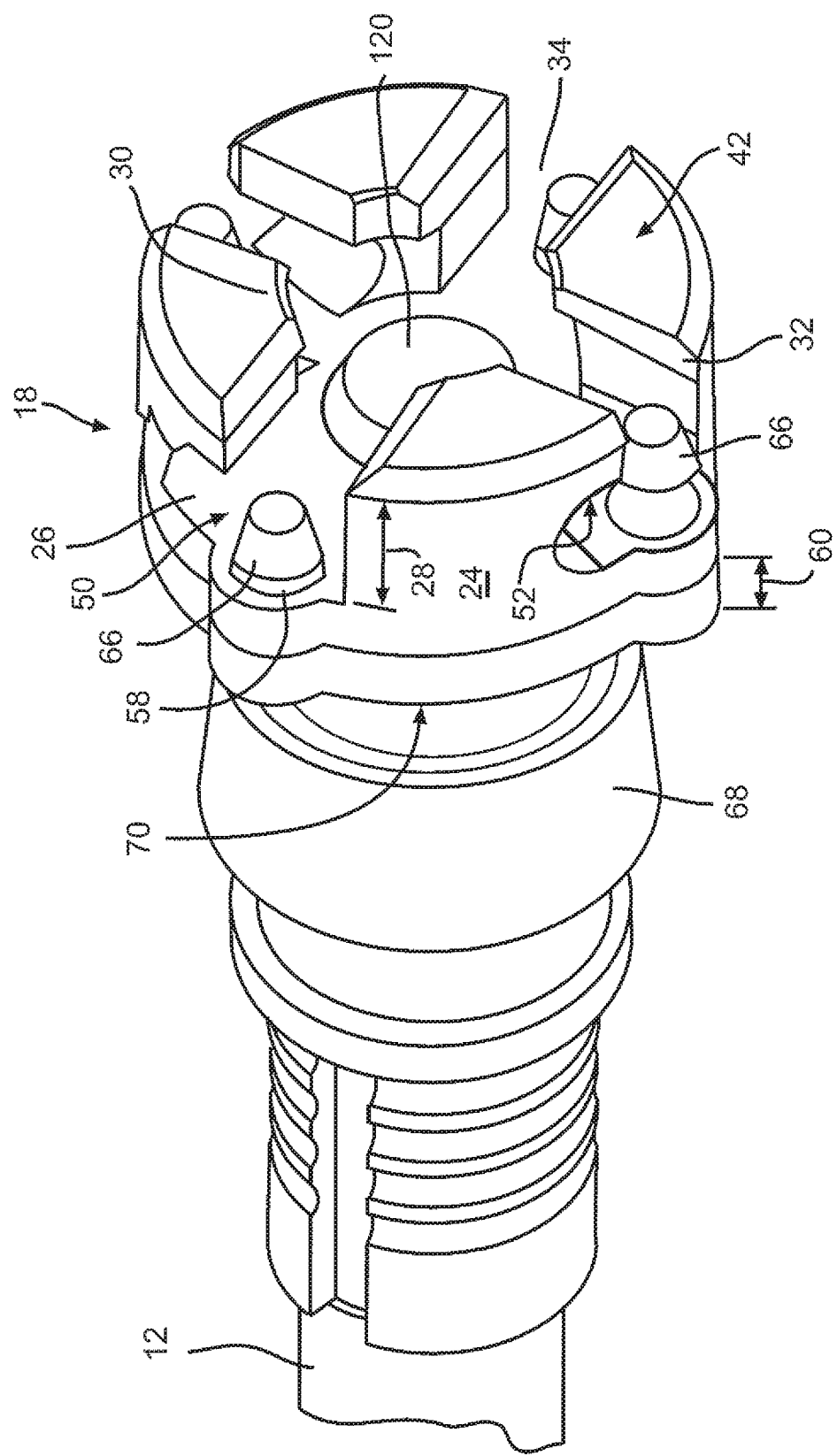
FIG. 2 is a magnified perspective view of an embodiment of a coupling for the surgical tool handle shown in FIG. 1.

As illustrated in FIGS. 2 and 3, the coupling 18 may comprise an overhang portion 30 that preferably extends from a distal end 32 of the sidewall 24. More preferably, the overhang portion 30 extends about perpendicular to the longitudinal axis A-A. In addition, each of the overhang portions 30 extends at least part way towards the longitudinal axis A-A.

Figure 4:
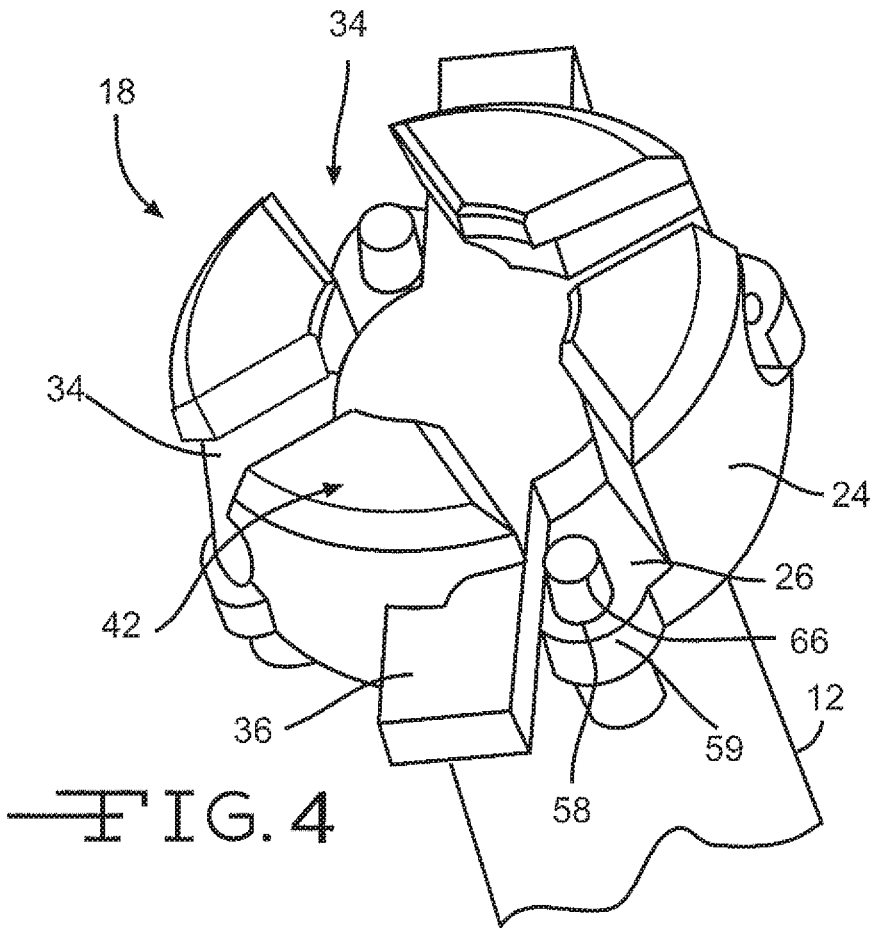
FIG. 4 is an enlarged perspective view of the coupling for the surgical handle shown in FIG. 3 having secured the attachment member of a rectangular cross-section in position.
Figure 4A:
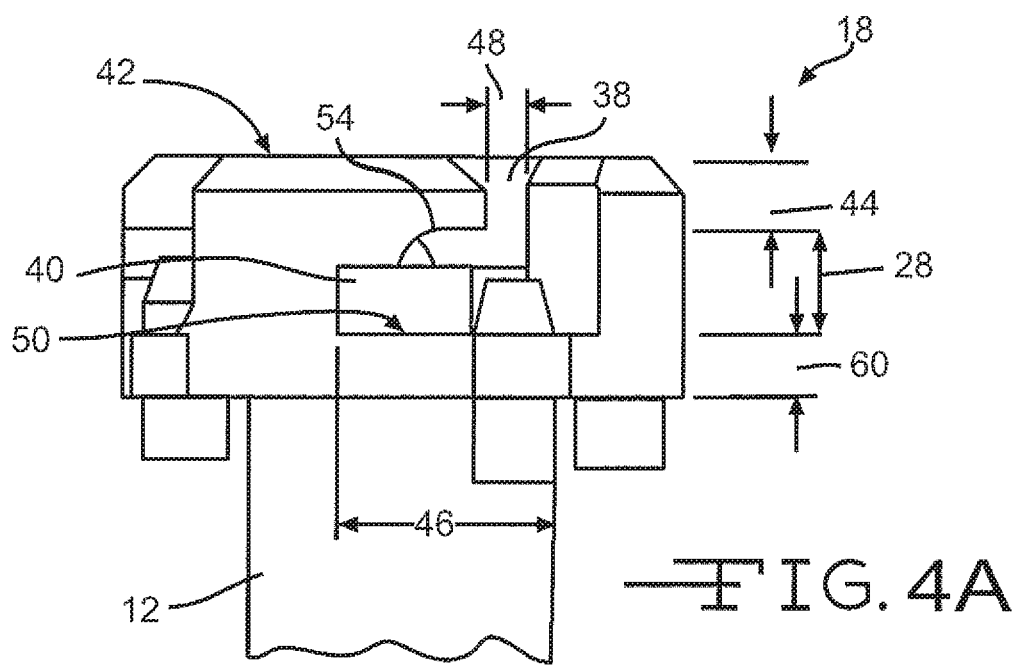
FIG. 4A is a side elevational view of the coupling for the surgical handle shown in FIG. 4.
Figure 5:
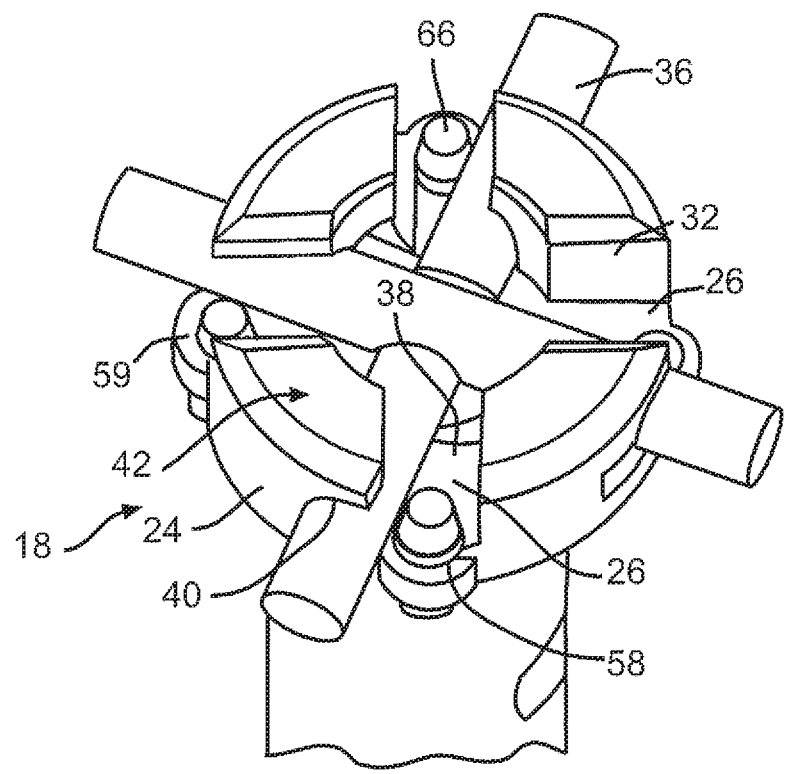
FIG. 5 is a perspective view of an embodiment of the coupling for the surgical handle shown in FIG. 1 receiving an attachment member of a curved cross-section.

As shown in FIGS. 2, 3, 3A, 4, 4A, 5 and 5A, a series of coupling grooves 34 extend through the sidewall 24 and the overhang 30 portions to provide a bayonet type fitting for connection to the attachment member 36 (FIGS. 1A, 1B and 3 to 5) of a surgical tool 22. In a preferred embodiment, each of the coupling grooves 34 comprises a first opening portion 38 positioned about perpendicular to a second opening portion 40. While four coupling grooves 34 spaced apart from each other by 90° are shown, it is contemplated by the present inventors that at least two diametrically opposed coupling grooves are needed to securely hold a reamer to the handle 10. More specifically, the first opening portion 38 extends from a top surface 42 of the coupling sidewall 24 through the overhang portion 30 and into open communication with the second opening portion 40. As shown in FIGS. 3 to 5, a height 44 of the first opening portion 38 extends about parallel to longitudinal axis A-A through the overhang portion 30 and may also extend at least part-way through the height of the sidewall 24 of the coupling 18. A width 46 of the second opening portion 40 of the coupling groove 34 extends through a width of the sidewall 24 and along at least a portion of the annular perimeter of the sidewall 24 extending from the coupling platform 26.

In a preferred embodiment, the width 46 of the second opening portion 40 is greater than a width 48 of the first opening portion 38. Each coupling groove 34 is constructed such that at least a portion of the attachment member 36 of a surgical tool 22 is first fitted through the first coupling groove opening portion 38 and then into the second groove opening portion 40. Once the attachment member 36 is positioned within the second opening 40, the tool 22 is then rotated either in a clockwise or counter clockwise direction about the longitudinal axis A-A to capture the attachment member 36 between a top surface 50 of the coupling platform 26 and a bottom surface 52 of the second opening portion 40. In a preferred embodiment, as illustrated in FIGS. 3 and 3A, the second opening portion 40 of the coupling groove 34 comprises a left side inlet 54 having a curved cross-section and a right side inlet 56 having a rectangular cross-section. Thus, a surgical tool 22 having an attachment member 36 of either a curved or rectangular cross-sectional geometry can be received and secured there within. As illustrated in FIGS. 3 and 3A, the cross-sectional geometries of the left and right side inlets 54, 56 may be interchangeable or reversed.

Therefore, to secure a surgical tool 22 having an attachment member 36 of either a curved or a rectangular cross-section to the handle 10, the tool is either rotated within the coupling 18 in a clockwise or counterclockwise manner. Likewise, to remove the surgical tool 22 from the coupling 18, the attachment member 36 is rotated in an opposite direction to that used to secure the tool to the coupling 18. For example, a surgical tool 22 having an attachment member 36 with a curved cross-section may be rotated in a clockwise manner to seat in the curved inlet 54 and a surgical tool 22 having a rectangular cross-section may be rotated in a counter-clockwise direction to seat in the rectangular inlet 56 of the second opening 40 within the coupling 18.

Figure 5A:
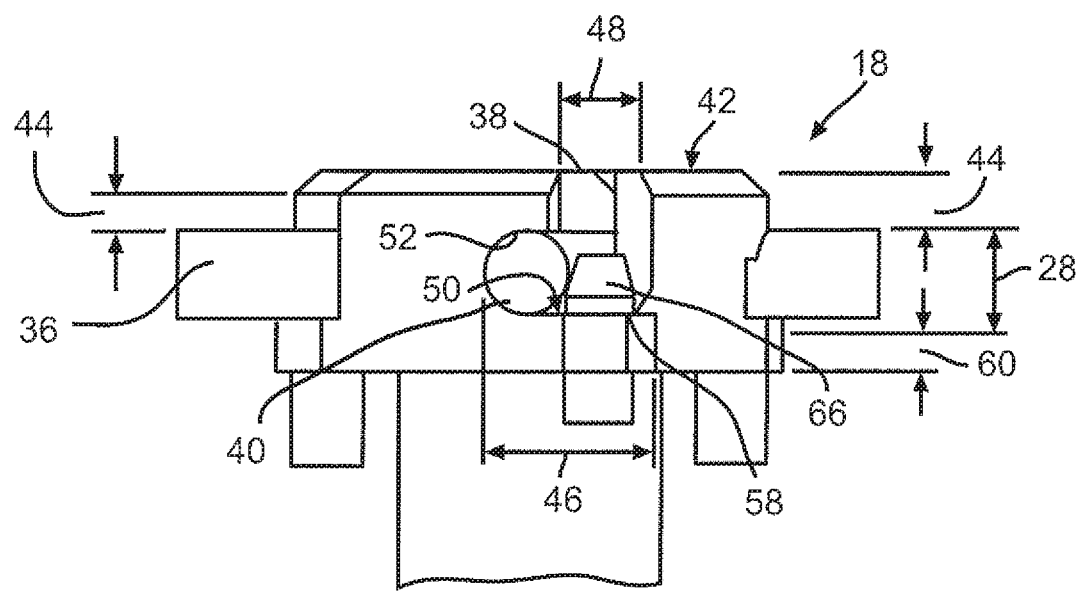
FIG. 5A is a side elevational view of the coupling for the surgical tool handle shown in FIG. 5.

FIGS. 2, 4, 4A, 5 and 5A illustrate embodiments of attachment couplings 18 having alternatively different second opening portion 40 geometries that may be utilized with the tool handle 10 of the present invention. More specifically, as illustrated in FIGS. 2, 5 and 5A, the second opening 40 of the coupling groove 34 may be constructed having only a curved inlet 54 (FIG. 3). Alternatively, as illustrated in FIGS. 4 and 4A, the second opening 40 of the coupling groove 34 may be constructed having a combined curved and rectangular cross-sectional inlet. As shown, the second coupling groove opening 40 transitions from an opening having a curved cross-sectional inlet portion to a rectangular cross-sectional inlet portion.

Figure 6:
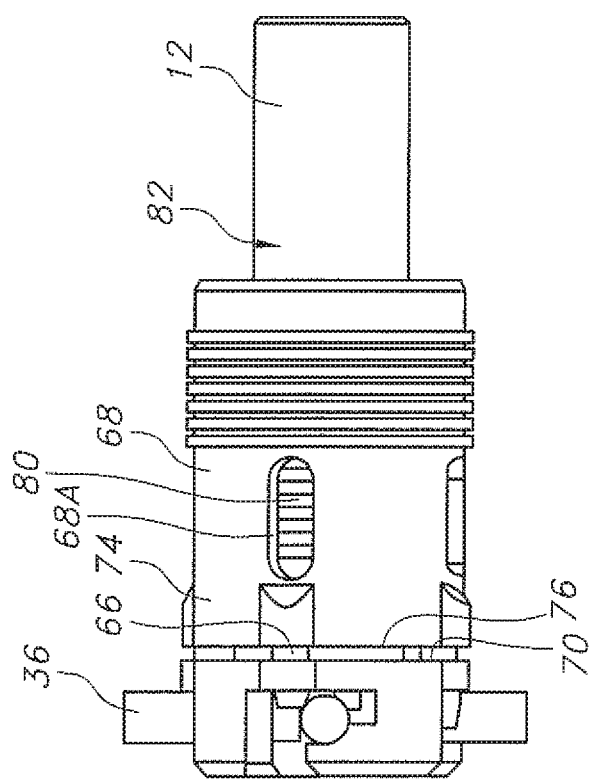
FIG. 6 is a side elevational view of the slidable collar residing at the distal portion of the surgical tool handle assembly of the present invention.
Figure 7:
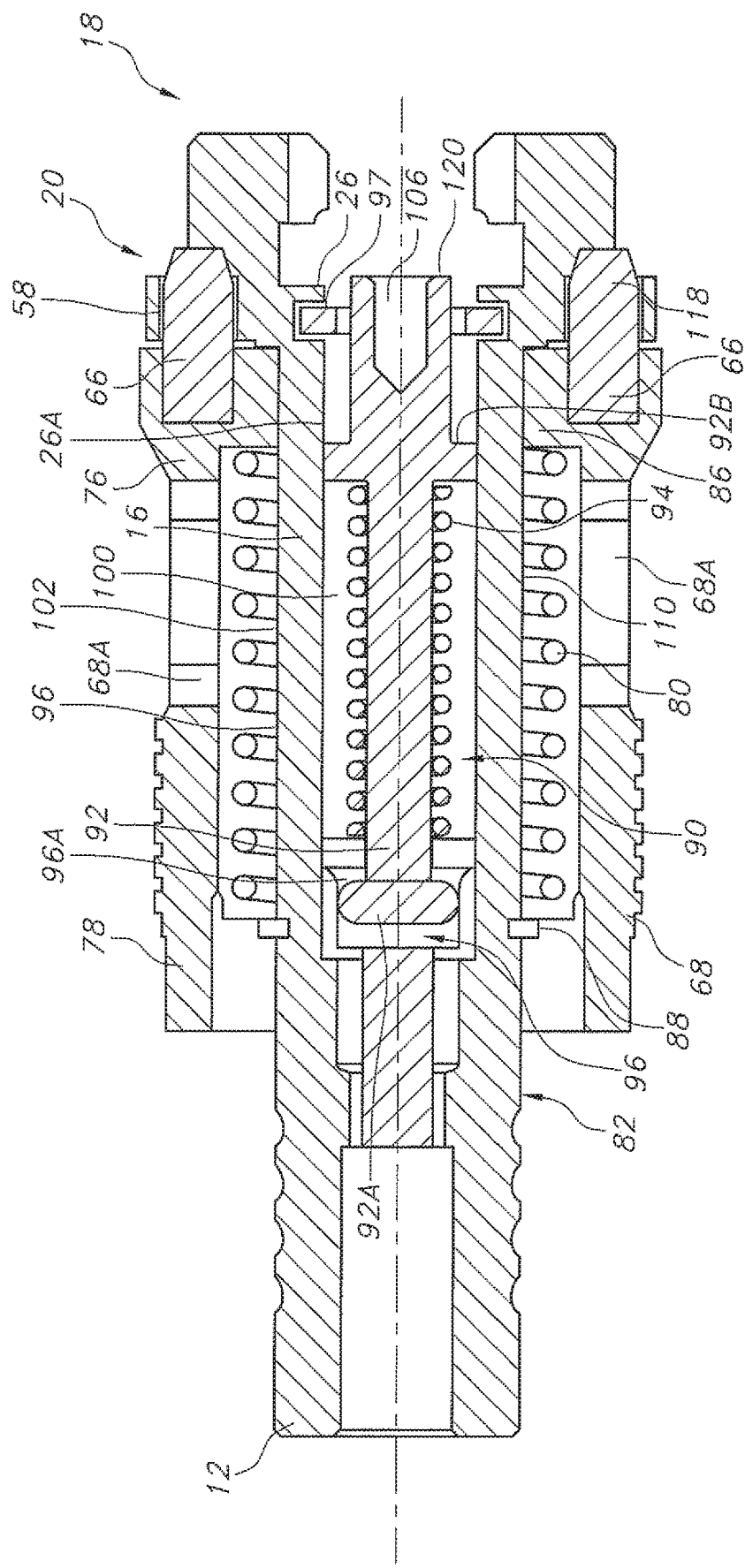
FIG. 7 is a cross-sectional view of the surgical tool handle assembly illustrated in FIG. 6.

In addition, a series of openings 58, preferably of a cylindrical shape, extend through a thickness 60 of the platform 26 of the coupling 18. In a preferred embodiment, a lobe portion 59 (FIGS. 4 and 5) projects outwardly from the outer perimeter of the platform 26. The lobe portion 59 provides an outward extension of the coupling platform in which at least one opening 58 extends therethrough as shown in FIGS. 1, 2, 4 and 5. A pin 66 preferably extends through each of the platform openings 58. As illustrated in FIGS. 1, 6 and 7, each of the collar pins 66 is secured within a slidable collar 68 that resides circumferentially around the shaft 12 and adjacent to a bottom surface 70 of the coupling platform 26. In a preferred embodiment, each of the pins 66 is positioned at a distal end 76 of the collar. The collar 68 further has a length that extends axially along the longitudinal axis A-A from a collar proximal end 78 to the collar distal end 76. The collar distal end 76 is contactable to the bottom surface 70 of the coupling platform 26.

As shown in FIGS. 6 and 7, a first bias member 80 resides between the shaft 12 and the collar 68. More specifically, the first bias member 80 resides between a distal lip portion 86 of the collar 68 and a first set ring 88 positioned circumferentially around an exterior surface 82 of the shaft 12 adjacent to the proximal collar end 78. As illustrated, the distal lip portion 86 extends about perpendicular from the interior surface of the collar 68. A gap between the end of the distal lip portion 86 and the exterior surface 82 of the shaft. 12 enables the collar 68 to slide axially in both a proximal and a distal direction along the shaft 12. As the collar 68 is slid in a proximal direction, the distal lip 86 compresses the first bias member 80 against the first set ring 88, thereby creating a bias force acting in the opposite, distal direction. When the collar 68 is released, this bias force moves the collar 68 and attached collar pins 66 in a distal direction towards the coupling platform 26. Once the collar 68 is released, the collar pins 66 preferably traverse into and through the openings 58 of the coupling platform 26 and into the second opening portion 40 (FIGS. 3A, 4A, 5 and 5A) of the coupling groove 34. In a preferred embodiment, each of the collar pins 66 secures the attachment member 36 of the surgical tool 22 within its respective curved or rectangular cross-sectional inlet 54, 56 of the second opening 40 of the coupling groove 34. More specifically, each of the collar pins 66 is designed to extend through the coupling platform 76 and into the opening 40 to block and thereby prevent movement of the attachment member 36 out of the correspondingly shaped inlet 54, 56 of the second opening 40.

As illustrated in FIGS. 6 and 7, in addition to the collar 68 and pins 66, the handle locking mechanism 20 comprises a locking piston subassembly 90. As illustrated, the locking piston subassembly 90 comprises a rod 92 extending to a proximal key 92A and a distal shoulder 92B. In a preferred embodiment, at least a portion of the locking piston subassembly 90 resides within the distal portion 16 of the shaft 12. More specifically, at least a portion of the locking piston subassembly 90 resides within a cylindrically-shaped cavity 100 extending axially along the distal end of the shaft 12. As shown in FIGS. 6 and 7, the rod 92 extends from the proximal key 92A to the distal contact plate 120 located distal to the distal shoulder 92B. The distal contact plate 120 has a socket 106. The proximal key 92A has, for example, an oblong shape provided with a lateral length that is significantly greater than its width with respect to the longitudinal axis A-A.

The proximal key 92A of the locking piston subassembly 90 is received in a key compartment 96 having an opening 96A that permits the proximal key to be moved axially out of the key compartment 96 using a hand tool (not shown) having a driver end that is matable with the socket 106. Likewise, the distal shoulder 92B abuts a distal lock ring 97 that is located proximal to the coupling platform 26. That way, when the driver end of the hand tool mated to the socket 106 is manipulated to rotate the locking piston subassembly 90 to align the proximal key 92A with the key compartment opening 96A, the distal shoulder 92B is permitted to move axially in a distal direction until the shoulder contacts lock ring 97.

Thus, with the driver end of the hand tool received in the socket 106, the hand tool is manipulated to rotate the rod 92 including the proximal key 92A so that the oblong shape of the key 92A matches the oblong shape of the key compartment opening 96A. In that manner, the locking piston subassembly 90 is partially movable out of the cylindrically-shaped cavity 100 extending axially along the distal end of the shaft 12 to facilitate cleaning the cavity 100 and the locking piston subassembly 90. Spaced apart openings 68A through the slidable collar 68 permit access between the shaft 12 and the collar for cleaning there.

As shown in FIG. 7, a second bias member 94 biases between the proximal key compartment 96 and the distal shoulder 92B of the locking piston subassembly 90. This biasing force causes the distal contact plate 120 provided with the socket 106 to extend distally and outwardly past the coupling platform. That way, when a surgical tool 22 having an attachment member 36 of a curved cross-section is seated in the curved inlet 54 or a surgical tool 22 having a rectangular cross-section is seated in the rectangular inlet 56 of the second opening 40 within the coupling 18, the distal contact plate 120 exerts an axial force against the attachment member to help secure the surgical tool in position received in the respective curved or rectangularly-shaped inlets 54, 56 of the second opening 40 of the coupling groove 34. This includes the respectively shaped curved or rectangular portions of the combined inlet shown in FIGS. 4 and 4A.

In operation, to engage the attachment member 36 of a surgical tool 22 within the coupling 18, the collar 68 is moved in a proximal direction away from the coupling platform 26. This action moves the collar pins 66 in a proximal direction, removing them from within the openings 58 of the coupling platform 26 so that the collar pins 66 do not protrude past the top surface 50 of the platform. Once the collar pins 66 are removed from the coupling platform 26, the attachment member 36 of the surgical tool 22 is positioned within the coupling grooves 34. First, the attachment member 36 is positioned through the first opening portion 38 and then within the second opening portion 40 of the coupling groove 34. In an embodiment, the attachment member 36 of the surgical tool 22 is preferably either rotated in a clockwise or counterclockwise manner depending upon the geometry of the cross-section of the attachment member, as previously discussed.

In a preferred embodiment, positioning the attachment member 36 within the coupling 18 forces the external surface of the attachment member 36 to act against the distal contact plate 120 of the locking piston subassembly 90, thereby proximally compressing the spring 94 within the cavity 100 of the shaft distal end 16. Simultaneously, the second bias member 94 provides a counter bias force acting against the attachment member 36 of the surgical tool 22. In a preferred embodiment, the second bias member 94 exerts an opposing force in a distal axial direction against the distal shoulder 92B, thereby exerting a force against at least a portion of the attachment member 36 of the surgical tool 22. Thus, movement and play of the surgical tool 22 within the coupling 18 is minimized.

After the attachment member 36 of the surgical tool 22 is positioned within the second opening 40 of the coupling groove 34, the collar 68 is released to move back to its original distal location. As the collar 68 is released, the bias force created by the first bias member 80 moves the collar pins 66 through the openings 58 of the coupling platform 26 of the coupling 18, thereby further securing the attachment member 36 and the surgical tool 22 within the handle assembly 10.

It is appreciated that various modifications to the invention concepts described herein may be apparent to those skilled in the art without departing from the spirit and the scope of the present invention defined by the hereinafter appended claims.

According to the present disclosure, a surgical tool handle is provided which is configured for connecting to a surgical tool, the surgical tool handle comprising:
a) a shaft comprising a shaft sidewall having a shaft length extending along a longitudinal axis from a shaft proximal end to a shaft distal portion having a shaft distal end, wherein the shaft has a shaft cavity comprising a cavity sidewall extending proximally from the shaft distal end part-way along the shaft length to a cavity end wall;
b) a coupling comprising an annular coupling sidewall extending distally from the distal shaft end, wherein at least two spaced apart coupling grooves extend proximally from a distal end of the coupling sidewall, each coupling groove comprising a primary axial inlet in open communication with a secondary inlet with at least a portion of the secondary inlet being radially offset from the primary inlet so that a distal portion of the coupling sidewall is aligned axially with respect to the secondary inlet;
c) a collar supported on the shaft in an axially movable relationship with respect to the shaft sidewall, the collar being proximal the coupling, wherein a distal end of the collar supports at least two distally extending collar pins;
d) a first coil spring extending from a first coil spring proximal end abutting a protrusion extending radially outwardly from the shaft sidewall to a first coil spring distal end abutting the collar, wherein with the first coil spring biasing the collar in a distal direction toward the coupling, the at least two collar pins extend through openings in the coupling to reside at least in part in the primary axial inlet of respective ones of the coupling grooves; and
e) a locking mechanism comprising:
  i) a rod received in the shaft cavity and extending from a rod proximal end to a distal contact plate; and
  ii) a second coil spring comprising a spring lumen receiving the rod, wherein the second coil spring extends from a second coil spring proximal end abutting a wall in the shaft cavity to a second coil spring distal end abutting a shoulder comprising the rod,
f) wherein the collar is manipulatable in a proximal direction against the bias of the first coil spring to remove the at least two collar pins from the coupling grooves, and
g) wherein a surgical tool is then manipulatable in an axial direction with respect to the longitudinal axis of the shaft to move an attachment member of the surgical tool into the primary inlets of the coupling grooves and then the surgical tool is rotatable in one of a clockwise or counterclockwise direction to position the attachment member in the secondary inlets of the coupling grooves with the second coil spring biasing the distal contact plate in a distal direction into contact with the surgical tool attachment member, and
h) wherein the collar is further manipulatable to permit the first coil spring to then bias the collar in a distal direction to position the at least two collar pins into the primary inlets of the respective coupling grooves with the distal portions of the coupling sidewall blocking the attachment member from moving axially out of the secondary inlets of the coupling grooves to thereby securely connect the surgical tool to the coupling of the surgical tool handle.

According to the present disclosure, the annular coupling sidewall extends distally from a coupling platform supported at the shaft distal end, and wherein the first coil spring biases the collar in the distal direction abutting the coupling with the at least two collar pins extending through the openings in the coupling platform so that the pins reside in the primary axial inlets of the coupling grooves.

According to the present disclosure, the first coil spring distal end abuts a distal collar lip extending radially inwardly toward the shaft sidewall.

According to the present disclosure, the distal contact plate is extendable outwardly past the shaft distal end of the shaft cavity.

According to the present disclosure, a key compartment resides in a proximal portion of the shaft cavity, and wherein the rod proximal end comprises a proximal key residing in the key compartment, and wherein the distal contact plate is manipulatable to rotate the rod about the longitudinal axis to align the proximal key with an opening in the key compartment so that the proximal key is removable from the key compartment to thereby at least partially remove the locking mechanism from the shaft cavity.

According to the present disclosure, the rod comprises a distal shoulder located proximal the contact plate, and the shaft supports a distal lock ring extending inwardly toward the longitudinal axis, and wherein, with the proximal key removed from the key compartment, the distal shoulder of the rod is configured to abut the lock ring to thereby prevent the locking mechanism from being completely removed from the key compartment.

According to the present disclosure, the at least two coupling grooves are diametrically opposed to each other.

According to the present disclosure, the at least two distally extending collar pins each have a respective pin axis aligned parallel to, but spaced from the longitudinal axis.

According to the present disclosure, the secondary inlet of each of the at least two coupling grooves is configured to receive a surgical tool attachment member of either a curved cross-section or a rectangular cross-section.

According to the present disclosure, the coupling comprises four spaced apart coupling grooves extending proximally from the distal end of the coupling sidewall.

According to the present disclosure, the four coupling grooves are spaced apart 90° from each other.

According to the present disclosure, the distal contact plate at the distal end of the rod comprises a socket.

According to the present disclosure, with a surgical tool connected to the coupling as the second coil spring biases the distal contact plate in the distal direction into contact with the surgical tool attachment member, the collar is manipulatable in a proximal direction against the bias of the first coil spring to remove the at least two collar pins from the respective coupling grooves, and wherein the surgical tool is then rotatable in the other of the clockwise or counterclockwise direction to move the attachment member from the secondary inlet and into the primary inlet of the coupling grooves, and then the surgical tool is further manipulatable in a distal direction with respect to the longitudinal axis of the shaft to move the attachment member out of the primary inlet of the coupling grooves to thereby disconnect the surgical tool from the surgical tool handle.

According to the present disclosure, the at least two coupling grooves are configured to connect to the attachment member of a surgical tool selected from the group consisting of a reamer, a rasp, and a patella cutter.

According to the present disclosure, a surgical tool handle is provided which is configured for connecting to a surgical tool, the surgical tool handle comprising:
a) a shaft comprising a shaft sidewall having a shaft length extending along a longitudinal axis from a shaft proximal end to a shaft distal portion having a shaft distal end, wherein the shaft has a shaft cavity comprising a cavity sidewall extending proximally from the shaft distal end part-way along the shaft length to a cavity end wall;
b) a coupling comprising an annular coupling sidewall extending distally from the shaft distal end, wherein at least two spaced apart coupling grooves extend proximally from a distal end of the coupling sidewall, each coupling groove comprising a primary axial inlet in open communication with a secondary inlet and a ternary inlet with at least a portion of the secondary and ternary inlets being radially offset in opposite directions with respect to the primary inlet so that distal portions of the coupling sidewall are aligned axially with respect to the secondary and ternary inlets, wherein the secondary inlet is configured to receive a surgical tool attachment member having one of a curved cross-section and a rectangular cross-section and the ternary inlet is configured to receive an attachment member of the other of the curved cross-section and the rectangular cross-section;
c) a collar supported on the shaft in an axially movable relationship with respect to the shaft sidewall, the collar being proximal the coupling, wherein a distal end of the collar supports at least two distally extending collar pins;
d) a first coil spring extending from a first coil spring proximal end abutting a protrusion extending radially outwardly from the shaft sidewall to a first coil spring distal end abutting the collar, wherein with the first coil spring biasing the collar in a distal direction toward the coupling, the at least two collar pins extend through openings in the coupling to reside at least in part in the primary axial inlet of respective ones of the coupling grooves; and
e) a locking mechanism comprising:
i) a rod received in the shaft cavity and extending from a rod proximal end to a distal contact plate; and
ii) a second coil spring comprising a spring lumen receiving the rod, wherein the second coil spring extends from a second coil spring proximal end abutting a wall of the shaft cavity to a second coil spring distal end abutting a shoulder comprising the rod,
f) wherein the collar is manipulatable in a proximal direction against the bias of the first coil spring to remove the at least two collar pins from the coupling grooves, and
g) wherein a surgical tool is then manipulatable in an axial direction with respect to the longitudinal axis of the shaft to move an attachment member of a surgical tool into the primary inlet of the coupling groove and then the surgical tool is rotatable in one of a clockwise or counterclockwise direction to position the attachment member in one of the secondary inlet and the ternary inlet of the coupling groove corresponding to a cross-sectional configuration of the attachment member with the second coil spring biasing the distal contact plate in a distal direction into contact with a proximal surface of the surgical tool attachment member, and
h) wherein the collar is further manipulatable to permit the first coil spring to then bias the collar in a distal direction to position the at least two collar pins into the primary inlets of the respective coupling grooves with the distal portion of the coupling sidewall blocking the attachment member from moving axially out of the secondary inlet or the ternary inlet of the coupling groove to thereby securely connect the surgical tool to the coupling of the surgical tool handle.

According to the present disclosure, with a surgical tool connected to the coupling as the second coil spring biases the distal contact plate in the distal direction into contact with the surgical tool attachment member, the collar is manipulatable in a proximal direction against the bias of the first coil spring to remove the at least two collar pins from the respective coupling grooves, and wherein the surgical tool is then rotatable in the other of the clockwise or counterclockwise direction to move the attachment member from the secondary inlet or the ternary inlet and into the primary inlet of the coupling grooves, and then the surgical tool is further manipulatable in a distal direction with respect to the longitudinal axis of the shaft to move the attachment member out of the primary inlet of the coupling grooves to thereby disconnect the surgical tool from the surgical tool handle.

According to the present disclosure, a surgical tool handle is provided which is configured for connecting to a surgical tool, the surgical tool handle comprising:
a) a shaft comprising a shaft sidewall having a shaft length extending along a longitudinal axis from a shaft proximal end to a shaft distal portion having a shaft distal end, wherein the shaft has an axial shaft cavity comprising a cavity sidewall extending proximally from the shaft distal end part-way along the shaft length to a cavity end wall;

b) a coupling comprising an annular coupling sidewall extending distally from a coupling platform supported at the shaft distal end, wherein four spaced apart coupling grooves extend proximally from a distal end of the coupling sidewall, the coupling grooves being spaced apart 90° from each other, and wherein each coupling groove comprises a primary axial inlet in open communication with a secondary inlet with at least a portion of the secondary inlet being radially offset with respect to the primary inlet so that a distal portion of the coupling sidewall is aligned axially with respect to the secondary inlet, wherein the secondary inlets of a first diametrically opposed pair of the four inlets is configured to receive a surgical tool attachment member having one of a curved cross-section and a rectangular cross-section and the secondary inlets of a second diametrically opposed pair of the four inlets is configured to receive a surgical tool attachment member having the other of the curved cross-section and the rectangular cross-section;

c) a collar supported on the shaft in an axially movable relationship with respect to the shaft sidewall, the collar being proximal the coupling, wherein a distal end of the collar supports four distally extending collar pins;

d) a first coil spring extending from a first coil spring proximal end abutting a protrusion extending radially outwardly from the shaft sidewall to a first coil spring distal end abutting the collar, wherein with the first coil spring biasing the collar in a distal direction toward the coupling, the four collar pins extend through openings in the coupling platform to reside at least in part in the primary axial inlet of respective ones of the coupling grooves; and e) a locking mechanism comprising:
  i) a rod received in the shaft cavity and extending from a proximal rod end to a distal contact plate; and
  ii) a second coil spring comprising a spring lumen receiving the rod, wherein the second coil spring extends from a second coil spring proximal end abutting the cavity end wall to a second coil spring distal end abutting a shoulder comprising the rod, f) wherein the collar is manipulatable in a proximal direction against the bias of the first coil spring to remove the four collar pins from the coupling grooves, and g) wherein a surgical tool is then manipulatable in an axial direction with respect to the longitudinal axis of the shaft to move an attachment member of the surgical tool into the primary inlets of either the first or second diametrically opposed pairs of the coupling grooves that has the secondary inlet configured to mate with either a curved cross-section or a rectangular cross-section of the attachment member of the surgical tool, and then the surgical tool is rotatable in one of a clockwise or counterclockwise direction to position the attachment member in the mating coupling grooves of the secondary inlets of the corresponding cross-sectional configuration with the second coil spring biasing the distal contact plate in a distal direction into contact with the surgical tool attachment member, and h) wherein the collar is further manipulatable to permit the first coil spring to then bias the collar in a distal direction to position the collar pins into the primary inlets of the respective coupling grooves with the distal portion of the coupling sidewall blocking the attachment member from moving axially out of the secondary inlets of the coupling grooves to thereby securely connect the surgical tool to the coupling of the surgical tool handle.

According to the present disclosure, with a surgical tool connected to the coupling as the second coil spring biases the distal contact plate in the distal direction into contact with the surgical tool attachment member, the collar is manipulatable in a proximal direction against the bias of the first coil spring to remove the at least two collar pins from the respective first or second diametrically opposed pairs of the coupling grooves, and wherein the surgical tool is then rotatable in the other of the clockwise or counterclockwise direction to move the attachment member from the secondary inlet and into the primary inlet of the coupling grooves, and then the surgical tool is further manipulatable in a distal direction with respect to the longitudinal axis of the shaft to move the attachment member out of the primary inlet of the coupling grooves to thereby disconnect the surgical tool from the surgical tool handle.

What is claimed is:

1. A surgical tool handle configured to connect to a surgical tool, comprising:
   a shaft extending along a longitudinal axis, wherein the shaft has a shaft cavity;
   a coupling disposed at a distal end of the surgical tool handle, the coupling comprising an annular coupling sidewall, wherein at least two spaced apart coupling grooves extend proximally from a distal end of the coupling, each coupling groove comprising a primary axial inlet in open communication with a secondary inlet, wherein, with respect to the longitudinal axis, at least a portion of the secondary inlet is offset radially from the primary axial inlet such that a distal portion of the coupling sidewall is aligned axially with the secondary inlet;
   a collar disposed on the shaft, wherein the collar is movable along the longitudinal axis with respect to the shaft, the collar being proximal the coupling, wherein the collar comprises at least two collar pins extending with the longitudinal axis;
   a first coil spring extending from a first coil spring proximal end abutting a protrusion of the shaft to a first coil spring distal end abutting the collar, wherein, with the first coil spring biasing the collar in a distal direction toward the coupling, each of the at least two collar pins being in an extended position in a respective one of the primary axial inlets of the coupling grooves;
   a locking mechanism comprising (i) a rod received in the shaft cavity and extending from a rod proximal end to a distal contact plate, and (ii) a second coil spring received in the shaft cavity with the rod, wherein the second coil spring extends from a second coil spring proximal end abutting a wall in the shaft cavity to a second coil spring distal end abutting a shoulder disposed on the rod, with the second coil spring biasing the distal contact plate in the distal direction; and
   wherein the collar is movable along the longitudinal axis in a proximal direction against the bias of the first coil spring to retract the at least two collar pins from the extended position in the primary axial inlets of the coupling grooves, and further movable along the longitudinal axis in the distal direction with the bias of the first coil spring to return the at least two collar pins to the extended position in the primary axial inlets of the coupling grooves.

2. The surgical tool handle of claim 1, wherein the coupling comprises a coupling platform and the annular coupling sidewall extends distally from a coupling platform, and wherein the first coil spring biases the collar in the distal direction abutting the coupling with the at least two collar pins extending through respective openings in the coupling platform to the respective one of the primary axial inlets of the coupling grooves.

3. The surgical tool handle of claim 1, wherein the first coil spring distal end abuts a distal collar lip extending radially inwardly toward the shaft sidewall.

4. The surgical tool handle of claim 1, wherein the distal contact plate is extendable outwardly past a distal end of the shaft cavity.

5. The surgical tool handle of claim 1, wherein a key compartment resides in a proximal portion of the shaft cavity, and wherein the rod proximal end comprises a proximal key residing in the key compartment, and wherein the distal contact plate is manipulatable to rotate the rod about the longitudinal axis to align the proximal key with an opening in the key compartment such that the proximal key is removable from the key compartment to at least partially remove the locking mechanism from the shaft cavity.

6. The surgical tool handle of claim 5, wherein the shoulder disposed on the rod is located proximal the distal contact plate, and the shaft supports a distal lock ring extending inwardly toward the longitudinal axis, and wherein, with the proximal key removed from the key compartment, the shoulder disposed on the rod is configured to abut the lock ring to prevent the locking mechanism from being completely removed from the shaft cavity.

7. The surgical tool handle of claim 1, wherein the at least two coupling grooves are diametrically opposed to each other.

8. The surgical tool handle of claim 1, wherein the at least two collar pins each have a respective pin axis aligned parallel to, but spaced from the longitudinal axis.

9. The surgical tool handle of claim 1, wherein the secondary inlet of each of the at least two coupling grooves is configured to receive a surgical tool attachment member of either a curved cross-section or a rectangular cross-section.

10. The surgical tool handle of claim 1, wherein the coupling comprises four spaced apart coupling grooves which extend proximally from the distal end of the coupling.

11. The surgical tool handle of claim 10, wherein the four coupling grooves are spaced apart 90° from each other.

12. The surgical tool handle of claim 1, wherein the distal contact plate comprises a socket.

13. The surgical tool handle of claim 1, wherein the at least two coupling grooves are configured to connect to an attachment member of a surgical tool.

14. The surgical tool handle of claim 1, wherein, when the collar is moved in the proximal direction against the bias of the first coil spring, the at least two collar pins retract from the primary axial inlets of the coupling grooves such that a surgical tool is then manipulatable along the longitudinal axis to move an attachment member of the surgical tool into the primary axial inlets of the coupling grooves and then the surgical tool is rotatable in one of a clockwise direction or a counterclockwise direction to position the attachment member in the secondary inlets of the coupling grooves with the second coil spring biasing the distal contact plate in the distal direction into contact with the surgical tool attachment member and the distal portions of the coupling sidewall aligned axially with the secondary inlets blocking the attachment member from moving axially out of the secondary inlets of the coupling grooves; and wherein, when the collar is further moved in the distal direction with the bias of the first coil spring, the at least two collar pins extend into the respective primary axial inlets of the coupling grooves such that the at least two collar pins block the attachment member from rotating out of the secondary inlets of the coupling grooves.

* * * * *